United States Patent

Munro et al.

Patent Number: 6,059,568
Date of Patent: May 9, 2000

[54] ORTHODONTIC BANDS

[76] Inventors: Donald Malcolm Munro, 6 Scott Street, Kew, Victoria 3101; Paul Simon Soon, 142 Winmallee Road, Balwyn Victoria 3103, both of Australia

[21] Appl. No.: 08/913,275

[22] PCT Filed: Mar. 8, 1995

[86] PCT No.: PCT/AU96/00131

§ 371 Date: Sep. 9, 1997

§ 102(e) Date: Sep. 9, 1997

[87] PCT Pub. No.: WO96/28112

PCT Pub. Date: Sep. 19, 1996

[30] Foreign Application Priority Data

Mar. 10, 1995 [AU] Australia .............. PN 1667

[51] Int. Cl.[7] ........................................... A61C 7/18
[52] U.S. Cl. .................................................... 433/23
[58] Field of Search ........................... 433/23, 2, 39

[56] References Cited

U.S. PATENT DOCUMENTS

| | | | |
|---|---|---|---|
| 436,972 | 9/1890 | Engei | 433/23 |
| 2,007,514 | 7/1935 | Boyd et al. | 433/23 |
| 2,378,279 | 6/1945 | Begg | 433/23 |
| 3,138,872 | 6/1964 | Lazarus | 433/23 |
| 4,167,813 | 9/1979 | Förster | 433/23 |
| 4,198,753 | 4/1980 | Förster | 433/23 |
| 4,260,374 | 4/1981 | Kurz . | |
| 4,669,979 | 6/1987 | Snead . | |
| 4,840,562 | 6/1989 | Wilson et al. | 433/23 |
| 5,257,439 | 11/1993 | LeBlanc | 433/23 |
| 5,697,783 | 12/1997 | Wilson et al. | 433/23 |

FOREIGN PATENT DOCUMENTS

| | | | |
|---|---|---|---|
| 13052/28 | 5/1928 | Australia . | |
| 107441 | 5/1938 | Australia . | |
| 115956 | 10/1941 | Australia . | |
| 136435 | 10/1946 | Australia . | |
| 33933/78 | 3/1978 | Australia . | |
| 38003/85 | 1/1985 | Australia . | |
| 2712446 | 9/1978 | Germany | 433/23 |

*Primary Examiner*—Ralph A. Lewis
*Attorney, Agent, or Firm*—Wallenstein & Wagner, Ltd.

[57] ABSTRACT

An orthodontic band (10) for placement on a molar tooth including a strip of flexible material (11), such as a stainless steel strip, having co-operating locking means (12, 13) located adjacent each end of the strip. Alternatively, the strip (6) may have an elongated tongue (62) formed at one end and slots (63, 64) for receiving the tongue at the other end. In use, the band is formed into a shape that will fit over a tooth and placed over the tooth. The band is then tightened to cause the band to closely fit to the tooth. An orthodontic cement is placed between the band and the tooth. The locking means (12, 13) on the band provides a frictional fit that may be sufficiently strong to hold the band in the desired configuration until the cement has set. Alternatively, the clamp may need to stay in place until the band and cement can provide a permanent set.

23 Claims, 4 Drawing Sheets

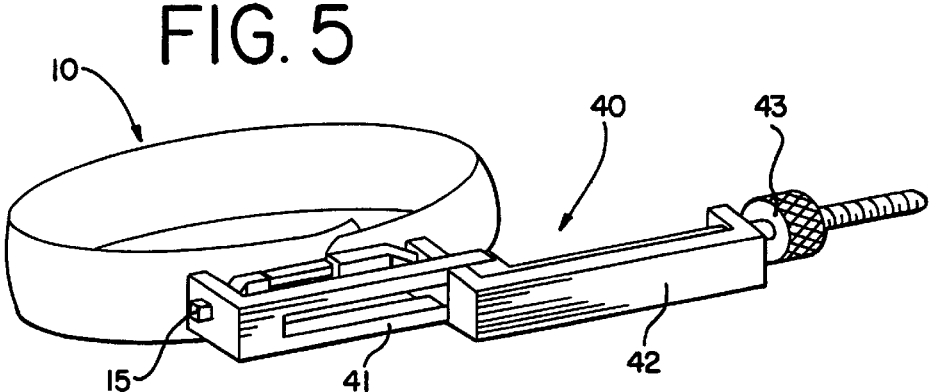
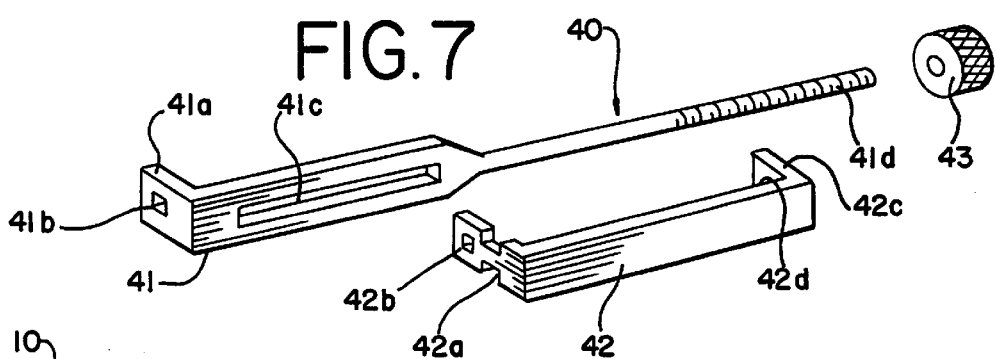
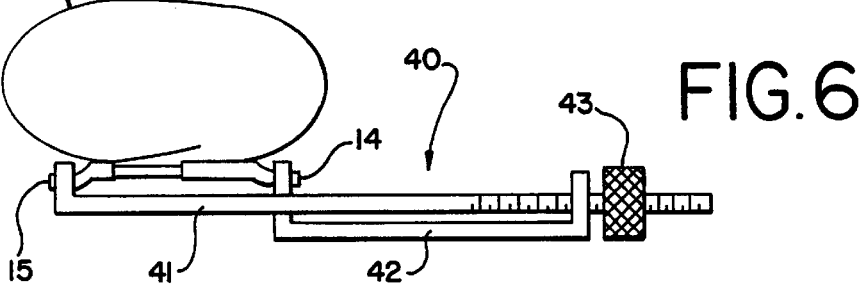
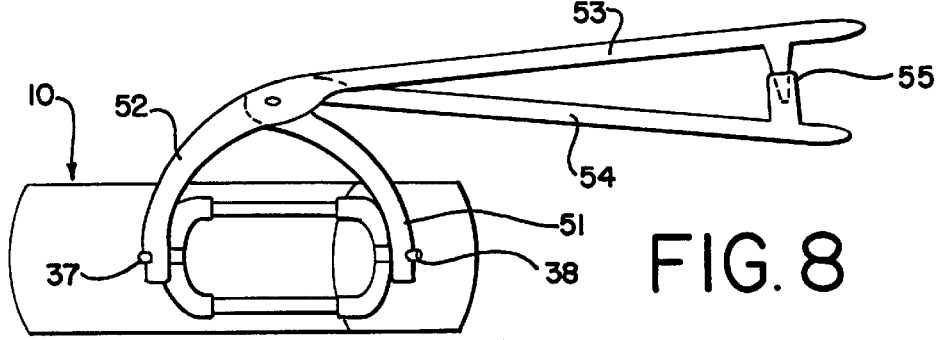

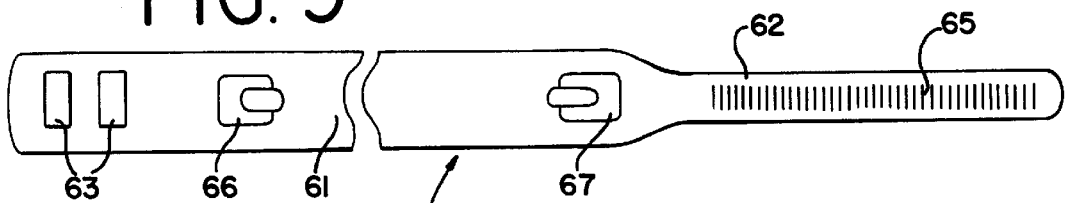
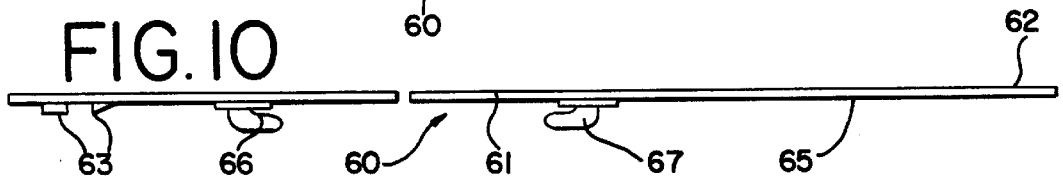
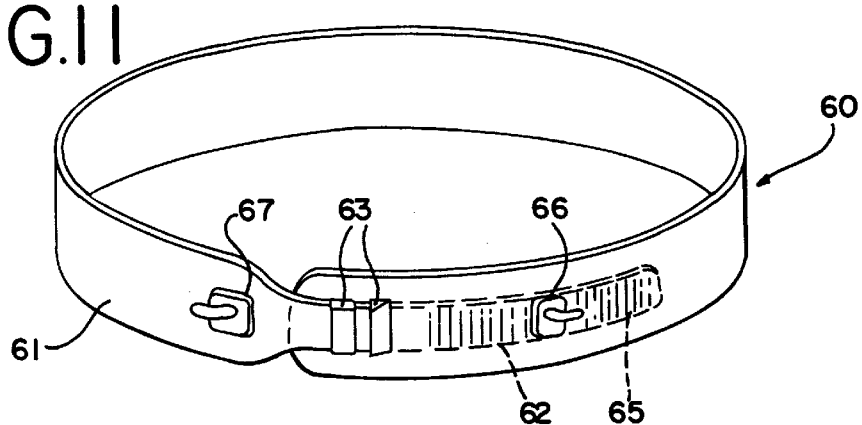
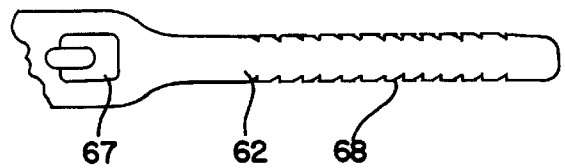
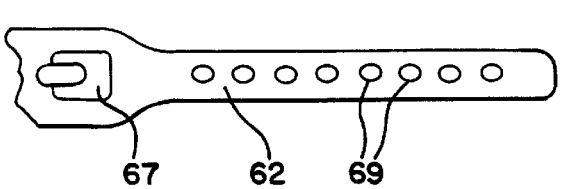
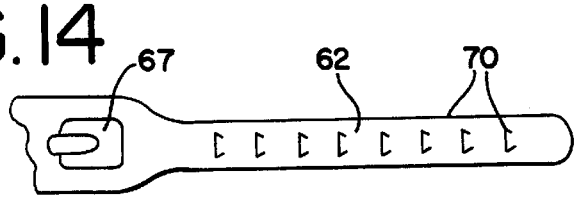

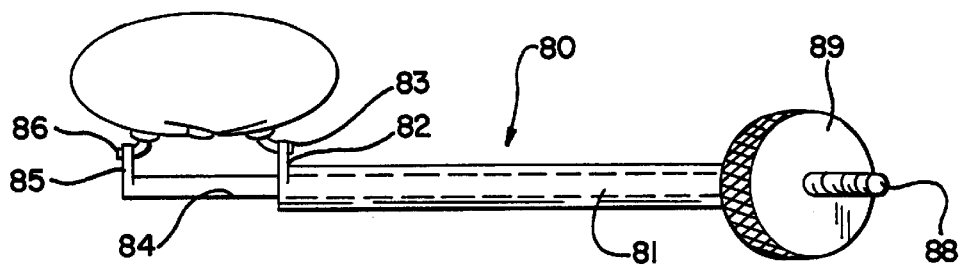
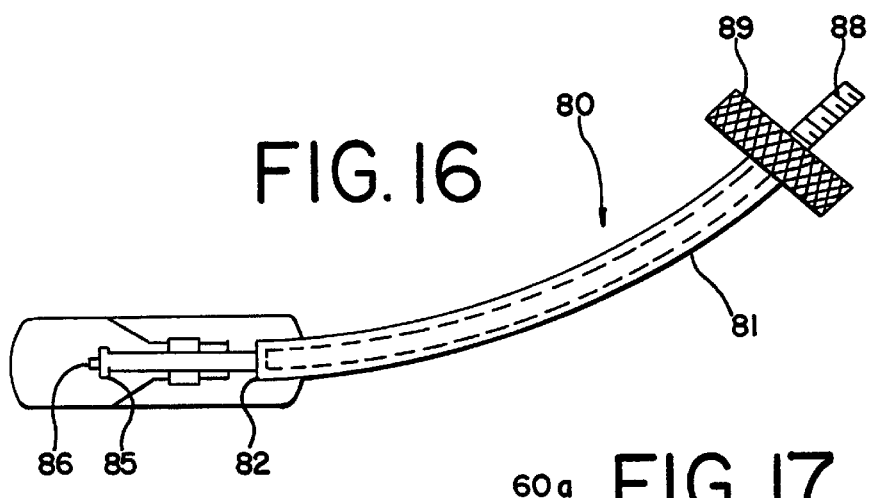
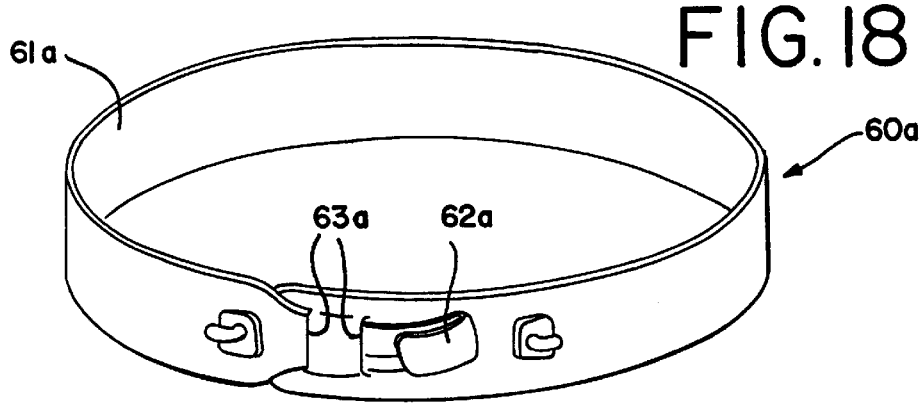

ORTHODONTIC BANDS

TECHNICAL FIELD

The present invention relates to orthodontic bands, and in particular to orthodontic bands for placement on molar teeth. The invention also relates to a method for placement of orthodontic bands on teeth.

BACKGROUND OF THE INVENTION

Fitment of braces to straighten the teeth of a patient involves a number of steps. In one procedure, the rear molar teeth are spread apart from each other by the use of spacers, such as plastic wedges, plastic O-rings or the like. After a period generally-ranging from a few days to a week, the spacers are removed from the gaps between the molar teeth and molar bands are placed over the molars and cemented into place. The molar bands usually have brackets welded or otherwise fixed thereon and these brackets provide an anchoring point for wires that pass through further brackets cemented to the front teeth. Tensioning the wire over a period of many months causes the teeth to straighten.

The bands fitted to the molar teeth play an important role in this orthodontic procedure because they provide the foundation upon which tension is applied to the wires on the teeth. Molar bands currently used comprise a closed ring of metal that has been shaped and sized to closely fit over each tooth. As the shape and size of the molar teeth can vary greatly from patient to patient and because the size of each molar tooth of any given patient may be different to the other molar teeth of that patient, orthodontists must maintain a large inventory of molar bands in order to be able to treat each patient. This obviously places an undesirable cost burden on the orthodontist.

Furthermore, placement of the molar bands onto the molar teeth can be difficult. The molar bands are cemented onto the teeth and are intended to remain on the teeth for many months and even for years. Therefore, it is critical that each band fit closely to its respective tooth and is properly cemented in place. Poor cementing may cause the band to work loose over time, necessitating replacement. More importantly, if the band does not fit closely to the tooth and an adequate spread of cement between the tooth and the band is not obtained, gaps may exist between the tooth and the band. Such gaps are potentially sites for serious tooth decay and must be avoided. Unfortunately, the method used for placing the band on a tooth, which involves coating the inside of the band with cement and then pushing the band onto the tooth, may leave areas where there is not sufficient cement to fully coat the tooth and the band.

SUMMARY OF THE INVENTION

The present invention provides an orthodontic band that is intended to overcome, or at least ameliorate, the above disadvantages.

In a first aspect, the present invention provides an orthodontic band for placement on a molar tooth comprising a strip of flexible material having co-operating locking means for holding means located at, adjacent, or near to each end of the strip of flexible material.

Throughout this specification, the term "locking means" and "holding means" are used to denote any co-operating means that can hold the band in a tightened state at least temporarily, preferably until cement applied to the tooth has substantially set.

Preferably, the locking means is a self locking device, such as a friction fit arrangement. Such locking devices limit reopening when in position and are self locking in that they lock when activated and require no adjustments other than correct fitting of the band. Examples of suitable devices for use as the locking means include a wire and tube arrangement in which a wire located at or near one end of the strip is adapted to be received in and held by a tube located at or near the other end of the strip. A ratchet mechanism, such as a saw-tooth extension receivable in a co-operable receiving means, may also be used. It will be appreciated that a large number of locking means other than those specifically described may be used in the present invention and the invention extends to cover all suitable locking means. It should be kept in mind that the preferred locking mechanisms are self locking and include one part located at or near one end of the strip and a co-operating other part located at or near the other end of the strip. A plurality of locking members may be employed, if desired.

In another aspect, the present invention provides an orthodontic band comprising a strip of flexible material including an elongate tongue at one end thereof and one or more slots or openings at or near the other end thereof, said slots adapted to receive said elongate tongue and wherein an end portion of said elongate tongue is positioned on the inside of the band when the tongue is passed through said slots or openings.

Preferably, the elongate extension includes means to increase the strength of a friction fit between the elongate extension and the one or more slots. This may comprise serrations or saw-teeth formed on the elongate extension, or a surface-roughened surface, for example, as may be formed by surface etching.

The orthodontic band of the present invention is intended to be placed on a tooth by shaping the band to a size and shape that is slightly larger than the tooth upon which it is to be placed. The band is subsequently placed over the tooth and tightened to fit snugly over the tooth. The band can be adjusted for size over a small range, thus accommodating a range of sizes of molar teeth. It is also envisaged that the band will be produced in three or four sizes per posterior tooth, ranging from small to large, in order to accommodate different patients having differently sized teeth (to other patients), Thus, the present invention may require that the orthodontist stock only three or four bands per posterior tooth, which is a great reduction compared to conventional closed ring bands currently used, it being noted that it is necessary to stock in excess of thirty bands per tooth with the current, closed-ring bands.

The orthodontic bands of the present invention may be made from any suitable material that is sufficiently flexible to allow the band to be correctly placed on the tooth. The material should also be sufficiently strong to provide a sound anchor for the wires of the braces. Metals and alloys that are used in the construction of current closed ring bands, such as various grades of stainless steel, are suitable for producing the orthodontic bands of the present invention.

Many orthodontic procedures utilize molar bands that incorporate lingual cleats and/or buccal brackets thereon. In an especially preferred embodiment of the invention the locking means of the orthodontic band also acts as the lingual cleat (s) or the buccal bracket(s). Alternatively, the band may be separately provided with lingual cleats or buccal brackets(s).

The orthodontic hand is preferably shaped to be contoured on its inner surface to enable the band to closely fit to the tooth. The contour may include a concave surface on the inner surface of the orthodontic band. Placement of the band on the tooth also involves the step of closing the locking mechanism by tensioning the band and this also causes the band to more closely conform to the outer profile of the tooth. Indeed, the band may be designed to undergo a small degree of plastic deformation when placed over the tooth and tensioned in order to ensure a close fit with the tooth.

Therefore, preferred embodiments of the band enable the band to adapt more closely superiorly and inferiorly than current closed ring bands and thus assist in obtaining an even layer of cement and a tight adaptation of the band to the tooth to lessen plaque accumulation and gingivitis This also assists in ensuring that the full width of the band is cemented to the tooth.

As a further advantage, the orthodontic band of the present invention permits an even spread of cementing medium between the tooth and the band. The fitting process involves shaping the band to a size just larger than the tooth to which it is to be fitted. Cement will then normally be placed on the inner surface of the band, or alternatively on the surface of the tooth (or both). The band is then fitted over the tooth. Because the band is slightly larger than the tooth, it easily fits over the tooth and minimizes the forcing of cement out from between the band and the tooth. Subsequent tightening of the band evenly spreads the cement.

The locking means used on the orthodontic band is not intended to hold the band firmly in place on the tooth during the entire period of treatment, which may range in time from months to years. Rather, it is the cement that firmly bonds the band to the tooth. The locking mechanism is intended to hold the band closed and under tension whilst the cement is setting. It will be appreciated, however, that the locking mechanism should preferably remain closed for the entire treatment period.

The present invention also provides a method for placement of an orthodontic band on a tooth.

In a second aspect, the present invention provides a method for placing an orthodontic band on a tooth comprising the steps of providing an orthodontic band comprising a strip of flexible material having co-operating locking means located at, adjacent, or near each end of the strip of flexible material, forming the orthodontic band into a shape that will fit over a tooth, placing the band over the tooth and tightening the band to cause the band to more closely conform to the shape of the tooth wherein an orthodontic cement is applied between the band and the tooth prior to tightening the band and the locking means holds the band in a closed, tightened configuration at least while the cement is setting.

The orthodontic cement may be applied between the band and the tooth by:

i) applying the cement to the inside surface of the band prior to placing the band on the tooth;

ii) applying the cement to the tooth prior to placing the band on the tooth; and/or iii) placing cement between the band and the tooth after the band has been placed on the tooth.

Method (i) is the preferred method for applying the cement.

The step of forming the band into a shape that will fit over the tooth preferably forms the band into a shape that is slightly larger than the tooth and then placing the band over the tooth If the band is shaped to be slightly larger than the tooth, the band will easily fit over the tooth and will not tend to force cement out of the space between the band and the tooth.

It is preferred that the step of shaping the band to fit over the tooth causes the locking means to interengage. Tightening of the band once it has been fitted over the tooth will then cause the locking mechanism to further interengage. It may also be possible that the locking mechanism may interengage only when the band is tightened.

The band may be placed from the lingual or palatal, in which case the locking means may advantageously incorporate or comprise the lingual cleats. This arrangement allows conventional buccal brackets to be placed on the band.

The band may also be designed to close on the buccal side, especially in the case of transpalatal appliances and this is advantageous in the placement of one side at a time. Typically, molar bands are provided with buccal brackets. The locking means of the present invention may comprise a buccal bracket when the band is placed on the tooth and the locking means closed, (i.e. the locking means forms the buccal bracket).

The band is preferably placed in position with an implement or tool which allows easy access to the tooth and direct placement with easy adjustment before final adaptation. The implement preferably includes a first arm adapted to receive a part of the locking mechanism located at or near one end of the strip and a second arm adapted to receive a part of the locking mechanism located at or near the other end of the strip, with the first arm being moveable relative to the second arm to allow adjustment or tightening of the band.

The implement may suitably comprise a pair of pliers or a clamp, especially a substantially linear clamp. Such a clamp is preferred because it allows easy access to the tooth and mouth.

Alternatively, the implement may comprise a generally cylindrical sleeve having a first holding means to hold part of the band, a shaft extending through the sleeve, the shaft having a second holding means for holding another part of the band and means to adjust the distance between the first holding means and the second holding means. Preferably, the first holding means and the second holding means engage respective lingual cleats on the band. Preferably, the generally cylindrical sleeve is arcuate in a longitudinal direction to improve access to the rear of the mouth.

In another aspect, the present invention provides an implement as hereinabove described. The implement may be used to position conventional molar bands or molar bands in accordance with the invention.

BRIEF DESCRIPTION OF DRAWINGS

The invention will now be further described with reference to the accompanying drawings, in which:

FIG. 5 shows a front view of a band held in position by a clamp and ready for placement on a tooth;

FIG. 6 is a plan view of FIG. 5;

FIG. 7 shows an exploded view of the clamp shown in FIGS. 5 and 6;

FIG. 8 shows a schematic view of a band held in position by a pair of pliers and ready for placement on a tooth.

FIG. 9 shows another embodiment of the present invention;

FIG. 10 shows a side view of FIG. 9;

FIG. 11 shows the band of FIG. 9 in a closed position;

FIGS. 12 to 14 show alternate details of the elongate extension of the band shown in FIG. 9;

FIG. 15 shows another implement for placing the band on the tooth;

FIG. 16 is a side view of FIG. 15;

FIG. 17 shows another band in accordance with the present invention; and

FIG. 18 is shows the band of FIG. 17 in a closed position.

DETAILED DESCRIPTION OF THE INVENTION

Figure 1:
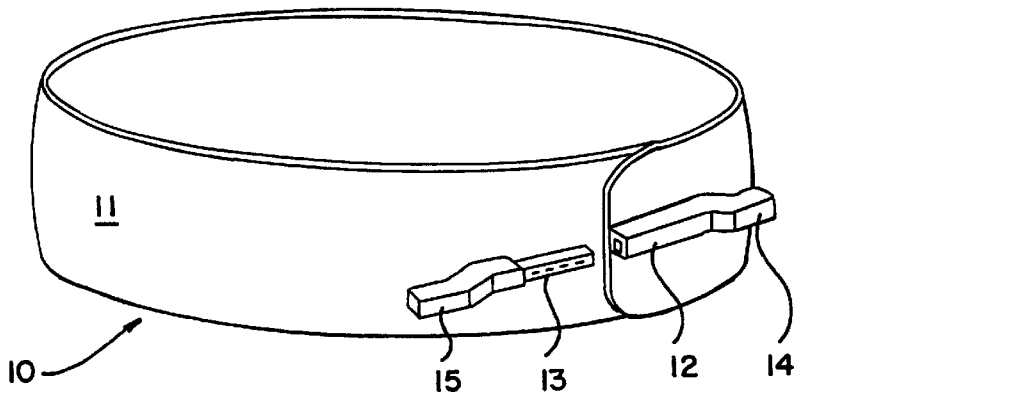
FIG. 1 shows a first embodiment of an orthodontic band in accordance with the present invention, with the band being in a closed position.

FIG. 1 shows an orthodontic band 10 comprising a strip of material 11, such as stainless steel, that is provided with a hollow tube 12 mounted at one end thereof and elongate rod member 13 mounted near the other end of the band. Ezod member 13 is adapted to be receivable in hollow tube 12. Both tube 12 and rod 13 include outwardly extending projections 14, 15, respectively which, in use, form the lingual cleat of the band. It will be appreciated that the band shows in FIG. 1 may be supplied in an open, flat position and that FIG. 1 shows the band shaped to fit over a tooth.

Figure 2:
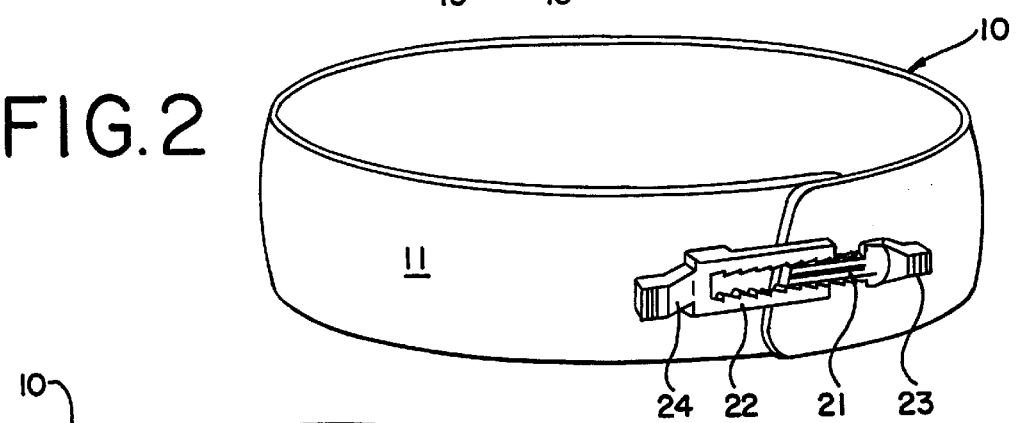
FIG. 2 shows another embodiment of an orthodontic band in accordance with the present invention.

The band 10 shown in FIG. 2 is generally similar to that shown in FIG. 1 but it incorporates a different locking mechanism. Specifically, the locking mechanism includes a sawtooth arrangement 21 that is adapted to be received within a corresponding sawtooth arrangement 22 mounted near the other end of the band. Insertion of sawtooth arrangement 21 into complementary sawtooth arrangement 22 causes the teeth of sawtooth arrangement 21 to interengage with the teeth at sawtooth arrangement 22 to thereby actuate the locking mechanism and close the band. Again, the locking mechanism of the band shown in FIG. 2 includes projections 23 and 24 that, in use, form the lingual cleat of the band.

Figure 3:
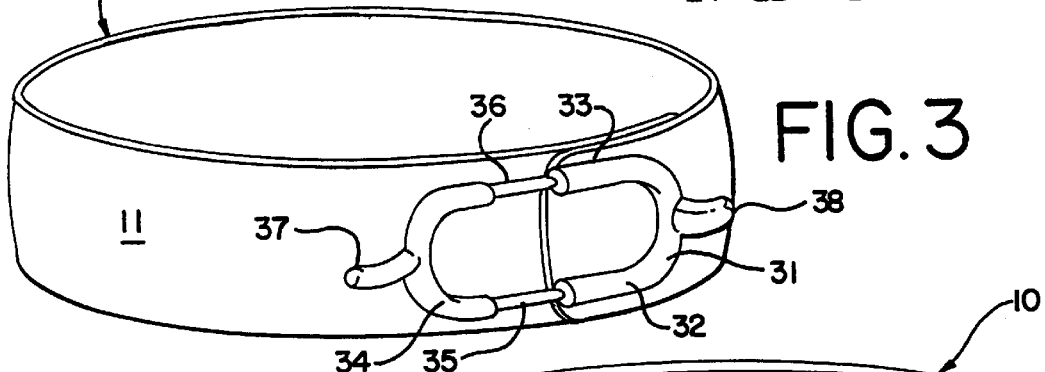
FIG. 3 shows a further embodiment of an orthodontic band of the present invention.
Figure 4:
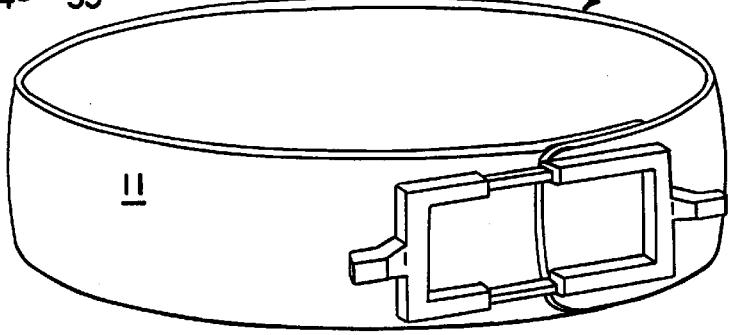
FIG. 4 shows yet another embodiment of an orthodontic band in accordance with the present invention.

FIGS. 3 and 4 also show bands that are generally similar to those shown in FIGS. 1 and 2 with slightly different locking arrangements. The locking mechanisms used on the band shown in FIGS. 3 and 4 are similar to the rod and tube arrangement shown in FIG. 1, but they incorporate a dual rod and tube arrangement. For example, the band 10 of FIG. 3 includes a first locking mechanism 31 having hollow tube extensions 32 and 33 A corresponding second part of the locking mechanism 34 includes rod extensions 35 and 36 that are adapted to fit into hollow tube extensions 32 and 33, respectively. Outward projections 37 and 38 formed with the locking mechanism are used to form the lingual cleat of the band. Alternatively, the band shown in FIG. 3 may be positioned on the tooth such that the looking mechanism forms the buckle bracket of the band.

The locking mechanism shown in the band 10 of FIG. 4 is generally similar to that shown in FIG. 3 but with detail differences in the design.

FIGS. 5 and 6 show one method of applying the band to the tooth. As can be seen from FIGS. 5 and 6, band 10 is formed into a shape that is slightly larger than the tooth. The band is held in this shape by inserting projections 14 and 15, which form the lingual cleat of the band into holes formed in arms 41 and 42 of clamp 40. Clamp 40 acts to hold the band in the desired shape and facilitates placing the band over the tooth. Once the band has been placed over the tooth (and the orthodontic cement has been placed between the tooth and the inner surface of the band) screw actuator 43 is used to close the arms of the clamps 41, 42 together. This acts to tighten the band and to place the band in tension. Once the band has been tightened to the required degree, the clamp in conjunction with the locking mechanism holds the band closed until the cement has fully set. The clamp is then removed.

Orthodontic band 10 should be of a length such that when placed on the tooth there is a small degree of overlap of the ends of the strip of material that forms the band. However, the degree of overlap should not be so large as to require trimming of excess length from the band once it is in place This assists in only having to place the band on the tooth a single time.

Although not clearly described, it is also generally necessary to separate the teeth prior to placing the band into position, as is conventional in current techniques.

FIG. 7 shows the clamp 40 used in the invention in greater detail. As can be seen, the clamp 40 includes a first arm 41 and a second arm 42. First arm 41 has an outwardly projecting and portion 41a having a hole 41b formed therein. Hole 41b is designed to accommodate projection 15 of the lingual cleat of the band. Arm 41 also includes a slot 41c that is designed to receive outward projection 42a of arm 42. Arm 42 can thereby longitudinally move along slot 41c. Arm 42 also includes hole 42b that can accept projection 14 of the lingual cleat. It can be seen that holes 41b and 42b provided in the arms 41 and 42 act to securely hold the band during placement and fitment of the band.

As can further be seen from FIG. 7, arm 41 also includes threaded portion 41d. In use, outward projection 42c of arm 42 is placed over the threaded portion 41d, with the threaded portion 41d passing through hole 42d formed in outward projection 42c. A threaded screw 43 is then placed on threaded portion 41d and threaded screw enables adjustment of the distance between outward projections 41a and 42a of arms 41 and 42 to be carried out.

FIG. 8 shows the use of plier to place the band on a tooth. The band shown in FIG. 8 is generally similar to that shown in FIG. 3. In FIG. 8, pliers 50 having arms 51 and 52 are used to engage lingual cleat projections 37 and 38 of the band. Actuation of the handles 53 and 54 enable adjustment of the tension on the band. The plier So may also include a ratchet mechanism 55 in order to hold the pliers in a desired position. In this regard, the pliers can act as clamping pliers.

FIGS. 9 and 10 show another band in accordance with the present invention. The band 60, for example, made of stainless steel, includes a main portion 61 and an elongate extension or tongue 62. Slots 63, are formed in one end of the hand 60. Elongate extension 62 is produced with serrations 65. In use, the band is formed around a tooth and elongate extension 62 passes through slots 63, as shown in FIG. 11. Serrations 65 act to increase the degree of friction fit between the elongate extension 62 and slots 63. The elongate extension 62 and slots 63, form corresponding locking means at either end of the band. Band 60 is also fitted with lingual cleats 66, 67.

FIGS. 12, 13 and 14 show alternative arrangements for increasing the friction between the elongate extension 62 and the slots 63. In FIG. 12, the elongate extension is provided with saw-teeth 68. In FIG. 13, a plurality of holes 69 are formed in the elongate extension 62. In FIG. 14, notches 70 are formed in the elongate extension 62.

The band of FIGS. 9 to 12 is preferably supplied in a partly closed form in which the elongate extension 62 is entered into slots 63. The band may then be positioned over a tooth and tightened.

Another device suitable for positioning the band on the tooth and tightening the band is shown in FIGS. 15 and 16.

This device 80 is a clamping implement that includes a generally cylindrical sleeve 81. As best shown in FIG. 16, sleeve 81 is curved to enable better access to the rear parts of the mouth. One end of sleeve 81 is fitted with a holder 82 for holding one of the lingual cleats 83 of the band. A shaft 84 passes through sleeve 81 Shaft 84 has a holder 85 at one end for holding the other lingual cleat 56 of the band. Holders 82 and 86 may simply comprise projections that fit into holes in the lingual cleats 82, 86. Other arrangements may also be used. Shaft 84 also has a screw-threaded end 88 extending from the other end of sleeve 81. Turn-wheel 89 is used to move shaft 84 into and out of the shaft 84.

In order to place the band on a tooth, the lingual cleats are held by holders 82, 85, as is shown in FIG. 15. The dentist places cement on the inside of the band and then places the band over the tooth. At this stage, the band fits loosely over the tooth, which allows for easy placement of the band Turn-wheel 89 is turned to close the distance between holders 82, 85, which acts to tighten the band over the tooth and cause the band to squeeze the cement such that it spreads evenly on the contact surface between the tooth and the band. Once tightened to the required degree, implement 80 is removed from the band. Frictional forces between the elongate extension and the slots hold the band in place until the cement has set.

As can be seen from FIGS. 11 and 15, the band is closed such that elongate extension 62 lies under the main body portion 61, Consequently, there is no necessity to trim any excess length of the elongate extension from the band. Moreover, the cement tends to surround the elongate extension and when the cement sets it establishes both an adhesive bond and a mechanical bond with the band. This is accentuated when the elongate extension is provided with saw-teeth, serrations, holes or notches, as shown in FIGS. 9 to 14, as the cement can more readily surround the elongate extension. For example, when the elongate extension has holes therein, the cement can flow through and fill the holes when the band is placed on the tooth. When the cement has set, the cement that has filled the holes effectively forms solid columns of set cement in the holes. To remove the band from the tooth requires that the adhesive bond between the band and the tooth be broken and the mechanical strength of the columns of set cement be overcome. Thus, the use of a band which, when applied to the tooth, has a part underlying the band, can result in a strong bond being established. The cement may be considered to either partially or fully encapsulate the underlying part of the band.

Although not clearly shown in FIGS. 9 to 16, the band preferably includes contoured sides such that the band will more closely fit with the side profile of the tooth. The band may be shaped such that the side wall thereof is concave inwardly. This ensures a better fit with the tooth and assists in obtaining an even bonding of all the side wall of the band to its respective tooth.

FIGS. 17 and 18 show another embodiment of the band. This embodiment is similar to the embodiment shown in FIGS. 9, 10 and 11, except that the band has only two slots 63*a*. In use, the elongate extension 62*a* may be passed through the slots and then folded back upon itself as shown in FIG. 18.

The band in accordance with the present invention may be simply made by stamping or cutting from sheets of appropriate metal alloy or other suitable material. The band is simple to fit and it is possible that a dentist will only have to stock three or four sizes of bands to fit the molar teeth of any patient. At present it is necessary to stock up to 30 or more differently sized bands to fit the teeth of all patients.

The present invention allows a variable and adjustable molar band to be placed on the tooth by use of a removable clamp, which greatly facilitates placement.

The clamp tightens the band so that cement is spread evenly and completely under the band. In preferred embodiments, the cement closely adapts to serrations, holes or roughening on the tongue (elongate extension) of the band so that when the cement has set it forms a secondary mechanical locking mechanism as well as an adhesive bonding mechanism.

The band, because it can be tightened on the tooth and does not require removal after size is determined, is able to more closely contour to the surfaces of the tooth both occlusally and gingivally.

Those skilled in the art will appreciate that the invention described herein is susceptible to variations and modifications other than those specifically disclosed. It is to be understood that the invention is considered to encompass all such variations and modifications that are all within its spirit and scope.

We claim:

1. An orthodontic band comprising a strip of flexible material having an inner surface and an opposing outer surface, said inner surface adapted to contact a surface of a tooth and said outer surface adapted to face outwardly from said surface of the tooth, said band including an elongate tongue at one end thereof and one or more slots or openings in the strip of material at or near the other end thereof, said one or more slots or openings extending through said strip from said inner surface to said outer surface, said one or more slots or openings adapted to receive said elongate tongue such that an end portion of said elongate tongue is passed through said one or more slots or openings.

2. An orthodontic band as claimed in claim 1 wherein the elongate tongue has serrations thereon for assisting in holding said elongate tongue in position after said elongate tongue has been passed through said one or more slots or openings.

3. An orthodontic band as claimed in claim 1 wherein the elongate tongue has saw-teeth for assisting in holding said elongate tongue in position after said elongate tongue has been passed through said one or more slots or openings.

4. An orthodontic band as claimed in claim 1 wherein the elongate tongue has one or more holes therein for assisting in holding said elongate tongue in position after said elongate tongue has been passed through said one or more slots or openings.

5. An orthodontic band as claimed in claim 1 wherein the elongate tongue has one or more notches for assisting in holding said elongate tongue in position after said elongate tongue has been passed through said one or more slots or openings.

6. An orthodontic band as claimed in claim 1 wherein the strip of material has two or more lingual cleats thereon.

7. An orthodontic band as claimed in claim 1 wherein the band is made from stainless steel.

8. A method for placing an orthodontic band on a tooth comprising the steps of providing an orthodontic band comprising a strip of flexible material having an inner surface and an opposing outer surface, said inner surface adapted to contact a surface of said tooth and said outer surface adapted to face outwardly from said surface of the tooth, said band having co-operating holding means located at, adjacent, or near each end of the strip of flexible material, the holding means including an elongate tongue at one end of the strip adapted to be received in one or more slots or openings in the strip of material at or near the other end of the strip, wherein said one or more slots or openings in said strip extend through said strip from said inner surface to said outer surface, forming the orthodontic band into a shape that will fit over a tooth, placing the band over the tooth and tightening the band to cause the band to more closely conform to the shape of the tooth wherein the method further includes the step of passing the elongate tongue through the one or more slots or openings such that an end portion of the elongate tongue lies between the tooth and the strip when the band is placed on the tooth and wherein an orthodontic cement is applied between the band and the tooth prior to tightening the band and the holding means holds the band in a closed tightened configuration at least while the cement is setting.

9. A method as claimed in claim 8 wherein the steps of placing the band on the tooth and tightening the band causes the cement to flow around the underlying part of the elongate tongue to form an adhesive bond and a mechanical bond with the end portion of the elongate tongue.

10. A method according to claim 9 wherein the underlying part of the elongated tongue has one or more holes therein and the cement flows through and fills the holes.

11. A method according to claim 9 wherein the underlying part of the elongate tongue has serrations, saw-teeth or notches and the cement flows around and fills the serrations, saw-teeth or notches.

12. A method according to claim 8 wherein the orthodontic cement is applied to the inside surface of the band prior to placing the band on the tooth.

13. A method according to claim 8 wherein the orthodontic cement is applied to the tooth prior to placing the band on the tooth.

14. A method according to claim 8 wherein the orthodontic cement is placed between the band and the tooth after the band has been placed on the tooth.

15. A method according to claim 8 wherein the step of tightening causes plastic deformation of the band to ensure the band closely fits the tooth.

16. A method according to claim 8 wherein the band is placed in position with an implement which includes a first arm having a first holding means for holding part of the band located at or near one end of the strip and a second arm having second holding means for holding another part of the band located at or near the other end of the strip, with the first arm being moveable relative to the second arm to allow adjustment or tightening of the band.

17. A method according to claim 16 wherein the implement comprises a pair of pliers.

18. A method according to claim 16 wherein the implement comprises a clamp.

19. A method according to claim 16 wherein the implement is retained until the cement has substantially set and thereafter the implement is removed from the band.

20. A method as claimed in claim 8 wherein the band is placed in position with an implement which comprises a generally cylindrical sleeve having a first holding means to hold part of the band, a shaft extending through the sleeve, the shaft having a second holding means for holding another part of the band and means to adjust the distance between the first holding means and the second holding means.

21. A method according to claim 20 wherein the first holding means and the second holding means engage respective lingual cleats on the band.

22. A method according to claim 20 wherein the generally cylindrical sleeve is arcuate in a longitudinal direction.

23. A method according to claim 20 wherein the implement is retained until the cement has substantially set and thereafter the implement is removed from the band.

* * * * *

UNITED STATES PATENT AND TRADEMARK OFFICE
CERTIFICATE OF CORRECTION

PATENT NO. : 6,059,568
DATED : May 9, 2000
INVENTOR(S) : Donald Malcolm Munro and Paul Simon Soon It is certified that error appears in the above-identified patent and that said Letters Patent is hereby corrected as shown below:

Column 5, Line 19, delete "Ezod" and insert therefor --Rod--

Column 6, Line 41, delete "So" and insert therefor --50--

Column 7, Line 7, delete "56" and insert therefor --86--

Column 9, Line 21, delete "elongated" and insert therefor --elongate--

Signed and Sealed this

Twenty-second Day of May, 2001

Attest:

NICHOLAS P. GODICI

Attesting Officer     Acting Director of the United States Patent and Trademark Office